(12) United States Patent
Ishii et al.

(10) Patent No.: US 6,267,774 B1
(45) Date of Patent: Jul. 31, 2001

(54) SURGICAL KNIFE

(75) Inventors: Shiro Ishii, Niigata; Masahiro Endo, Seki, both of (JP)

(73) Assignee: Kai R&D Center Co., Ltd., Gifu-ken (JP)

(*) Notice: Subject to any disclaimer, the term of this patent is extended or adjusted under 35 U.S.C. 154(b) by 0 days.

(21) Appl. No.: 09/287,690

(22) Filed: Apr. 6, 1999

(51) Int. Cl.[7] .................................................. A61B 17/32
(52) U.S. Cl. .............................................. 606/167; 606/19
(58) Field of Search ..................... 30/346.55, 346.56; 606/167, 107, 126, 169, 159, 119, 121, 125; 604/19, 22

(56) References Cited

U.S. PATENT DOCUMENTS

| | | | |
|---|---|---|---|
| 4,037,322 | 7/1977 | Bresler | 30/53 |
| 4,922,614 * | 5/1990 | Machida | 606/167 |
| 4,985,034 * | 1/1991 | Lipton | 606/167 |
| 5,085,663 | 2/1992 | Tarr | 606/172 |
| 5,261,922 * | 11/1993 | Hood | 606/167 |
| 5,317,938 * | 6/1994 | De Juan et al. | 76/104.1 |
| 5,609,603 | 3/1997 | Linden | 606/177 |

FOREIGN PATENT DOCUMENTS

| | | |
|---|---|---|
| 52113588 | 9/1977 | (JP) . |
| 54-75888 | 6/1979 | (JP) . |
| 3-85010 | 8/1991 | (JP) . |
| 8215202 | 8/1996 | (JP) . |

* cited by examiner

Primary Examiner—Glenn K. Dawson
(74) Attorney, Agent, or Firm—Sheridan Ross PC

(57) ABSTRACT

A scalpel suitable for Caesarian sections and myometrium sections. The scalpel includes two sides, an edge, a back, and a curved tip. Projections and recesses are alternately formed along the edge. Sharp edges are formed on the projections or the recesses.

5 Claims, 4 Drawing Sheets

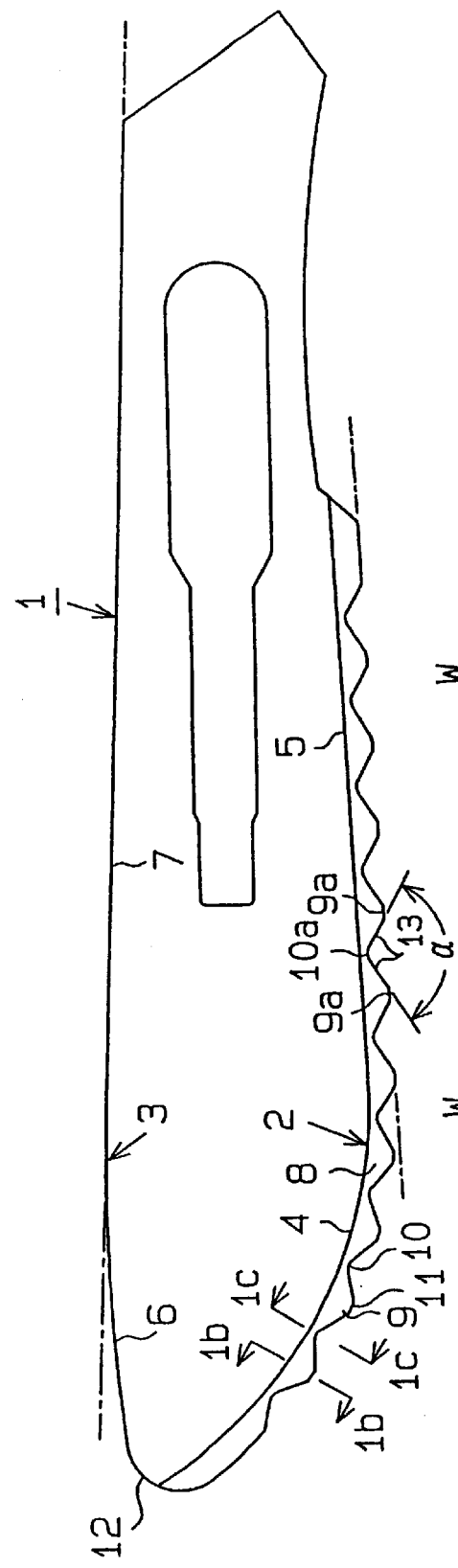
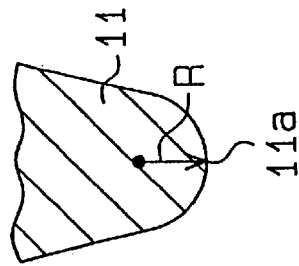
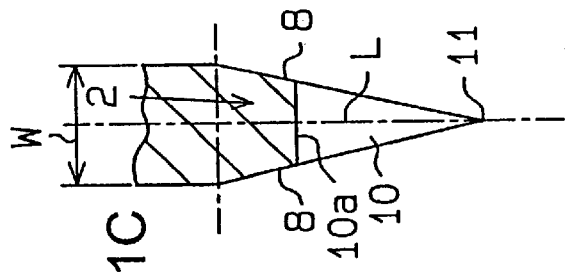
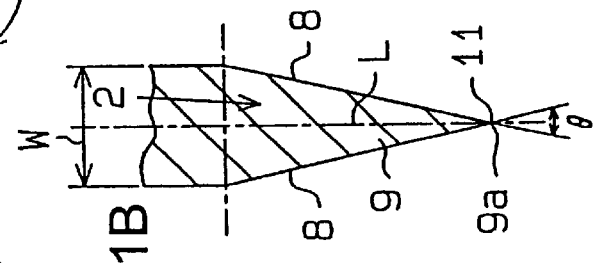

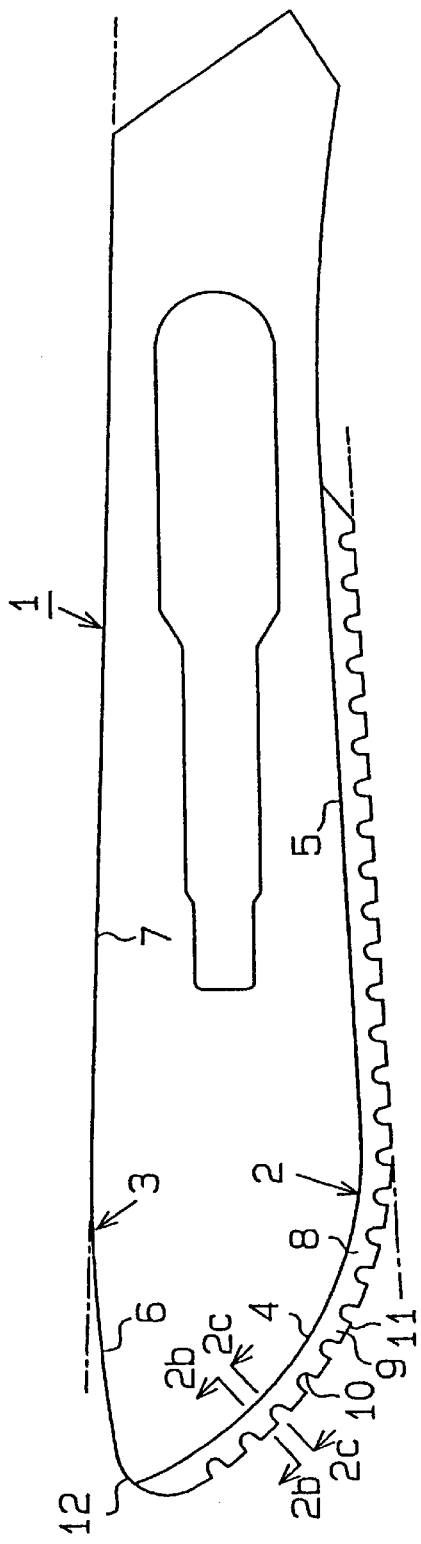
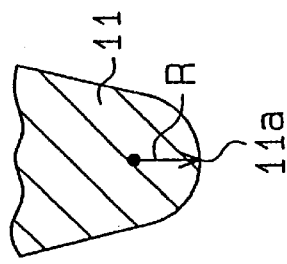
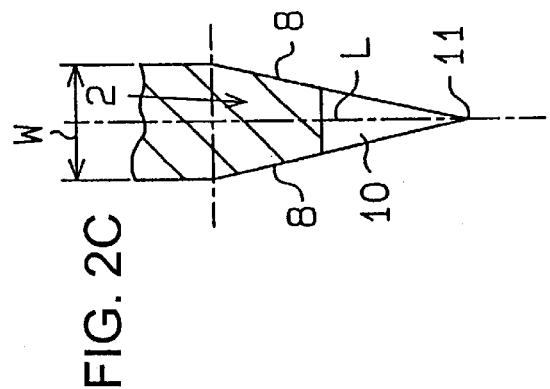
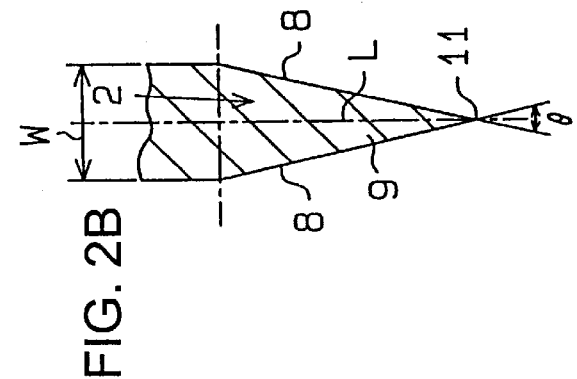

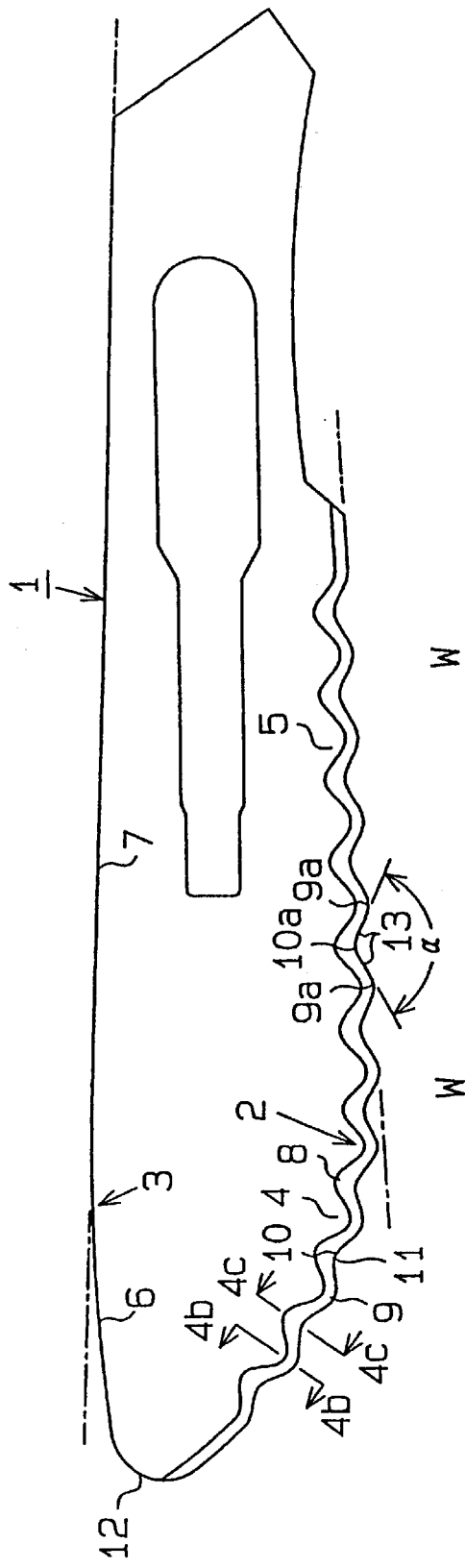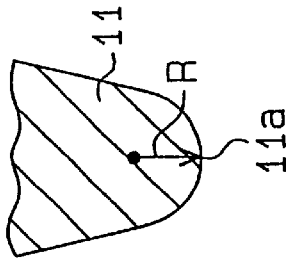

SURGICAL KNIFE

BACKGROUND OF THE INVENTION

The present invention relates to a surgical knife or a scalpel especially intended for Caesarian sections or myometrium sections.

Generally, scalpels are required to have a sharp edge. However, in Caesarian section or myometrium section, an egg membrane covering a fetus may be mistakenly cut by a scalpel having too sharp an edge. Therefore, scalpels having too sharp an edge are not suitable for Caesarian section or myometrium section. Accordingly, it is necessary to dull an edge of scalpels to a certain extent for such operations.

SUMMARY OF THE INVENTION

An objective of the present invention is to provide a scalpel that can cut a muscle layer but is not likely to cut an egg membrane.

To achieve the above objective, the present invention provides a scalpel having a first outer edge, a second outer edge located opposite to the first outer edge and two sides defined within the first and second outer edges. The tip of the scalpel is formed along with a curved line that connects the first outer edge to the second outer edge. A plurality of projections and recesses are alternately formed along the first outer edge. And a sharp edge is formed on the projections or the recesses.

Other aspects and advantages of the present invention will become apparent from the following description, taken in conjunction with the accompanying drawings, illustrating by way of example the principles of the invention.

BRIEF DESCRIPTION OF THE DRAWINGS

The features of the present invention that are believed to be novel are set forth with particularity in the appended claims. The invention, together with objects and advantages thereof, may best be understood by reference to the following description of the presently preferred embodiments together with the accompanying drawings in which:

FIG. 1(*a*) is a front view of a blade of a scalpel according to a first embodiment of the present invention;

FIG. 1(*b*) is a cross sectional view taken on line 1*b*—1*b* of FIG. 1(*a*);

FIG. 1(*c*) is a cross sectional view taken on line 1*c*—1*c* of FIG. 1(*a*);

FIG. 1(*d*) is an enlarged cross sectional view of the edge of FIG. 1(*b*);

FIG. 2(*a*) is a front view of a blade of a scalpel according to a second embodiment;

FIG. 2(*b*) is a cross sectional view taken on line 2*b*—2*b* of FIG. 2(*a*);

FIG. 2(*c*) is a cross sectional view taken on line 2*c*—2*c* of FIG. 2(*a*);

FIG. 2(*d*) is an enlarged cross sectional view of the edge of FIG. 2(*b*);

FIG. 3(*b*) is a front view of a blade of a scalpel according to a fourth embodiment;

FIG. 4(*a*) is a front view of a blade of a scalpel according to a fifth embodiment;

FIG. 4(*b*) is a cross sectional view taken on line 4*b*—4*b* of FIG. 4(*a*);

FIG. 4(*c*) is a cross sectional view taken on line 4*c*—4*c* of FIG. 4(*a*); and FIG. 4(*d*) is an enlarged cross sectional view of the edge of FIG. 4(*b*).

DETAILED DESCRIPTION OF THE PREFERRED EMBODIMENTS

First Embodiment

Figure 3A:
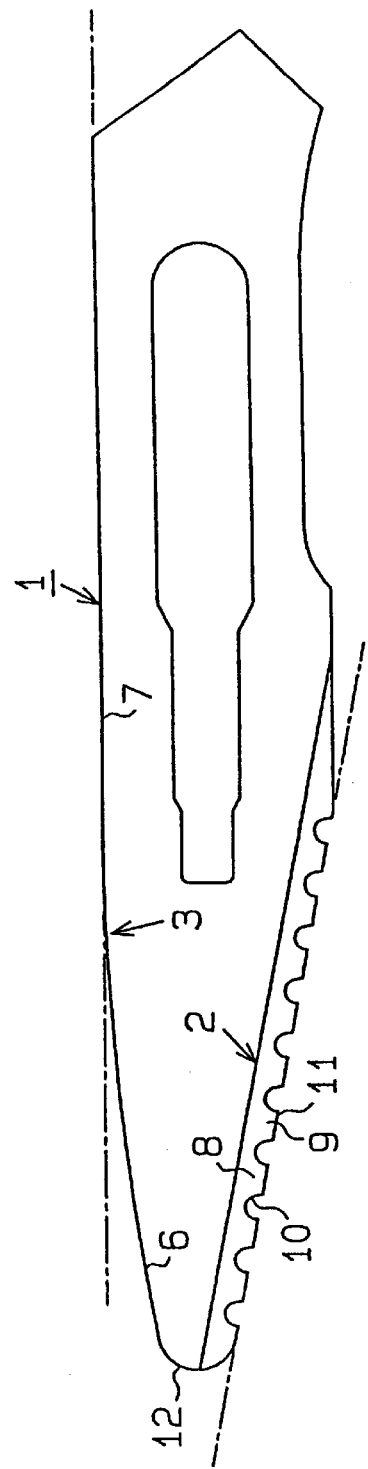
FIG. 3(*a*) is a front view of a blade of a scalpel according to a third embodiment.

A scalpel according to a first embodiment of the present invention will now be described in reference to FIG. 1. A blade 1 is attached to a handle (not shown). The blade 1 includes a tip 12, peripheral edge 2, and a back 3. The edge 2 and the back 3 are joined at the tip 12. The tip 12 is gently curved, and the radius of curvature of the tip 12 is arbitrarily determined. The edge 2 includes a curved part 4, which leads to a linear part 5. The back 3 includes a curved part 6, which leads to a linear part 7. As shown in FIGS. 1(*b*) and 1(*c*), inclined surfaces 8 are formed on both sides of the edge 2. Each inclined surface 8 is inclined equally (by an angle θ/2) with respect to a line L that bisects the blade 1. Projections 9 and recesses 10 are formed on the edge 2 at equal intervals. The projections 9 have the same height. As shown in FIG. 1(*a*), each projection 9 has a linear top 9*a* and a predetermined length. The linear tops 9*a* extend in the direction of the edge 2. A sharp edge 11 is formed on each linear top 9*a*. The sharp edge 11 is not formed on the tip 12.

In the present embodiment, the angle θ between the inclined surfaces 8 is twenty-seven degrees. The angle θ determines the sharpness of the scalpel. That is, the smaller the angle θ is, the sharper the scalpel is, and the greater the angle θ is, the duller the knife is. Therefore, for the proper sharpness, the angle θ is preferably in the range of ten to fifty degrees and more preferably in the range of fifteen to thirty-five degrees.

Further, as shown in FIG. 1(*d*), the end 11*a* of each sharp edge 11 is curved. The shape of the end 11*a* affects the sharpness of the scalpel. To achieve the proper sharpness, the radius of the curvature of the end 11*a* is within the range of 0.2 to 20 μm, and more preferably, 0.5 to 10 μm.

The diagonal lines 13 connect the tops 9*a* to the bottoms 10*a* of each recess. Adjacent diagonal lines 13 form an angle α, which is 120 degrees. The angle α is preferably in the range of sixty to 120 degrees, and more preferably, sixty to ninety degrees.

The scalpel according to the first embodiment has the following advantages.

scalpel of the first embodiment is used for cutting muscle layer in Caesarian section of myometrium section without mistakenly cutting an egg membrane.

The sharp edge 11 is formed only on the projections 9. Accordingly, the total length of the sharp edges 11 is shorter than the sharp edge of prior art scalpels. Therefore, the scalpel of the first embodiment is properly dulled.

Since the sharp edges 11 are arranged at equal intervals, the sharp edges 11 of an arbitrary part of the edge 2 is used for cutting an object. Therefore, a predetermined sharpness is maintained at any part of the edge 2.

Since the tip 12, which is most likely to contact the object to be cut, is curved, the possibility of mistakenly cutting an egg membrane is reduced. The sharp edge 11 is not formed on the tip 12, thus further reducing the chance of inadvertently cutting the egg membrane.

The angle θ of the sharp edge 11 is determined within the range from ten to fifty degrees, and the radius R is set within the range of 0.2 to twenty μm, which results in the proper sharpness of the scalpel.

If the angle α between the two adjacent diagonal lines 13 is determined in a proper range (sixty to 120 degrees), the end 11a of the sharp edge 11 is not likely to be caught in the object being cut, which results in smoother cutting.

FIGS. 2(a) to 2(d) show a blade 1 according to a second embodiment. As in the first embodiment, the blade 1 of the second embodiment includes a curved tip 12, sharp edges 11. each projection 9 has a linear top. Each recess 10 is semicircular. The sizes of each projection 9 and each recess 10 are smaller compared to the first embodiment. Accordingly, the interval between the projections 9 and the recess 10 is smaller and the number of projections 9 is greater compared to the first embodiment. The blade 1 of the second embodiment has the same advantages as the first embodiment.

FIG. 3(a) shows a blade 1 according to a third embodiment. The blade 1 includes a curved tip 12 and sharp edges 11. As in the second embodiment, the blade includes projections 9 having linear tops and semicircular recesses 10. The edge 2 is straight. The shape of the cross-sectional area of each sharp edge 11 is the same as that of the second embodiment of FIGS. 2(b) to 2(d).

Figure 3B:
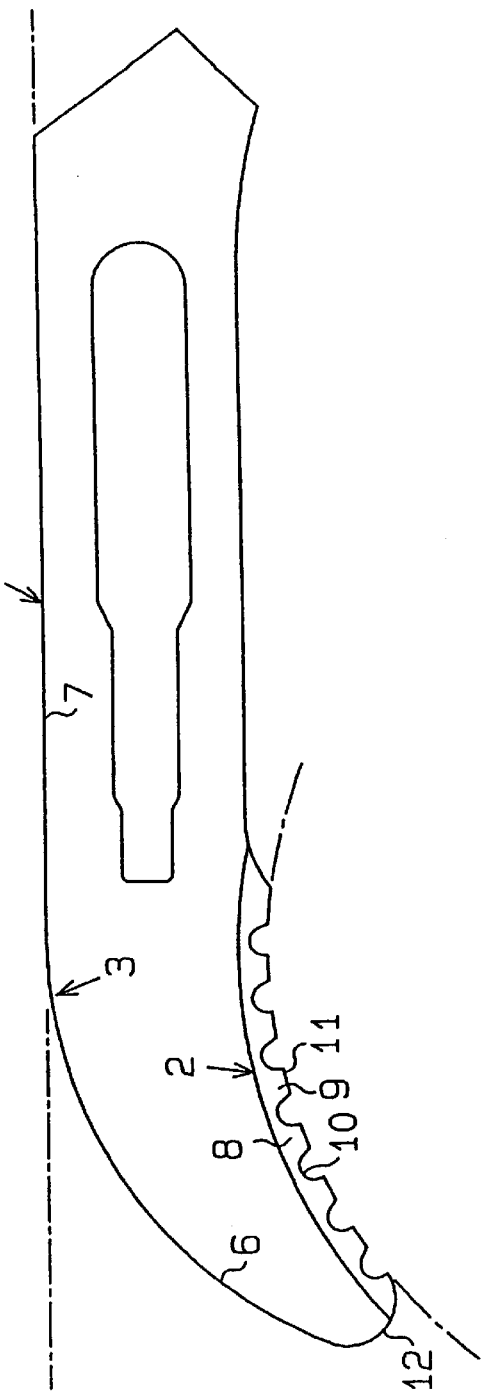

FIG. 3(b) shows a curved blade 1 according to a fourth embodiment. The blade 1 includes a curved tip 12 and sharp edges 11. As in the second embodiment, the blade 1 includes projections 9 having linear tops and semicircular recesses 10. The shape of the cross-sectional area of the edge 2 is the same as that of the second embodiment shown in FIGS. 2(b) to 2(d).

FIG. 4(a) shows a blade a according to a fifth embodiment. The fifth embodiment will now be described with regard to the differences from the first embodiment. A peripheral edge 2, which is wave-like, includes projections 9 and recesses 10, which are alternately formed. A sharp edge 11 is formed only in the vicinity of the bottom 10a of each recess 10. As shown in FIG. 4(d), the end 11a of each sharp edge 11 is curved, and the radius R of the curvature is set between 0.2 to twenty μm. As shown in FIG. 4(c), the angle θ is set between ten to fifty degrees. The angle α between inclined lines 13 is about 120 degrees. In the blade 1 of the fifth embodiment, the sharp edge 11 cuts an object only when the object contacts the recess 10. Since the blade 1 has to be pressed against an object to cut it, the chance of inadvertently cutting an object such as an egg membrane is reduced.

The first through third embodiments may be varied as follows.

The sharp edge 11 may be formed on both the projections 9 and the recesses 10.

In the blade 1 shown in FIG. 3(a) or FIG. 3(b), the size and shape of the projections 9 and the recesses 10 may be formed similar to those of the first embodiment.

In any of the first to third embodiments, the number, shape and size of the projections 9 and the recesses 10 and the total length of the sharp edges 11 may be varied.

It should be apparent to those skilled in the art that the present invention may be embodied in many other specific forms without departing from the spirit or scope of the invention. Therefore, the present examples and embodiments are to be considered as illustrative and not restrictive and the invention is not to be limited to the details given herein, but may be modified within the scope and equivalence of the appended claims.

What is claimed is:

1. A scalpel comprising:
    a back;
    an edge having a distal end;
    a curved tip, wherein the edge and the back are joined at the tip;
    a plurality of alternating projections and recesses located along the edge, wherein a sharp edge is formed on a distal portion of a plurality of the projections or the recesses, wherein said edge having a distal end has a pair of inclined surfaces, said inclined surfaces being joined by a curved surface having a radius of curvature in the range of 0.2 to twenty μm.

2. A Caesarian section and myometrium section scalpel comprising:
    a back;
    an edge having a distal end;
    a curved tip, wherein the edge and the back are joined at the tip;
    a plurality of alternating projections and recesses located along said edge having a distal end, wherein a sharp edge is formed on a distal portion of a plurality of the projections or the recesses;
    wherein said edge having a distal end is tapered and has a pair of inclined surfaces that are joined together at said distal end, said inclined surfaces are joined by a curved surface having a radius of curvature in the range of 0.2 to twenty μm.

3. The scalpel according to claim 2, wherein said recesses have sides and the angle between the sides of each recess is in the range of 60 to 120 degrees.

4. The scalpel according to claim 2, wherein the projections are uniform and each have a linear distal end.

5. A scalpel comprising:
    a back;
    an edge having a distal end;
    curved tip, wherein the edge and the back are joined at the tip; and
    a plurality of uniformly alternating projections and recesses located along the edge, wherein the distal end of the edge has alternating sharp and relatively dull sections such that either the projections or the recesses have the relatively dull sections and the other have the sharp sections, wherein said edge having a distal end has a pair of inclined surfaces joined by a curved surface having a radius of curvature in the range of 0.2 to twenty μm.

* * * * *